US008945609B2

(12) United States Patent
Schuetz et al.

(10) Patent No.: US 8,945,609 B2
(45) Date of Patent: *Feb. 3, 2015

(54) THERMOSETTING NEUTRALIZED CHITOSAN COMPOSITION FORMING A HYDROGEL, LYOPHILIZATE, AND PROCESSES FOR PRODUCING THE SAME

(75) Inventors: Yannic Schuetz, Troistorrents (CH); Virginie Caratti-Besson, Morges (CH); Oliver Jordan, Prangins (CH); Robert Gurny, Geneva (CH)

(73) Assignee: Laboratoire Medidom S.A., Geneva (CH)

( * ) Notice: Subject to any disclaimer, the term of this patent is extended or adjusted under 35 U.S.C. 154(b) by 1498 days.

This patent is subject to a terminal disclaimer.

(21) Appl. No.: 12/158,467

(22) PCT Filed: Dec. 23, 2005

(86) PCT No.: PCT/EP2005/013980
§ 371 (c)(1),
(2), (4) Date: Jun. 20, 2008

(87) PCT Pub. No.: WO2007/073749
PCT Pub. Date: Jul. 5, 2007

(65) Prior Publication Data
US 2009/0004230 A1 Jan. 1, 2009

(51) Int. Cl.
*A61L 15/00* (2006.01)
*C08L 5/08* (2006.01)
(Continued)

(52) U.S. Cl.
CPC . *C08L 5/08* (2013.01); *A61L 15/00* (2013.01); *A61K 9/0019* (2013.01);
(Continued)

(58) Field of Classification Search
CPC .................................................. A61L 15/00
USPC .................................................. 424/445
See application file for complete search history.

(56) References Cited

U.S. PATENT DOCUMENTS 5,541,304 A * 7/1996 Thompson ...................... 536/20
5,550,187 A   8/1996 Rhee et al.
(Continued)

FOREIGN PATENT DOCUMENTS

JP   2001-513367 A    9/2001
JP   2003-321398      11/2003
(Continued)

OTHER PUBLICATIONS

Chenite et al., Novel Injectable Neutral Solutions of Chitosan Form Biodegradable Gels in situ, Biomaterials, Elsevier Science Publis., Nov. 1, 2000, pp. 2155-2161, vol. 21.
(Continued)

*Primary Examiner* — Benjamin Packard
(74) *Attorney, Agent, or Firm* — Faegre Baker Daniels LLP

(57) ABSTRACT

The aqueous thermosetting neutralized chitosan composition, forming a phosphate-free transparent hydrogel at a temperature higher than 5° C., comprises 0.1 to 5.0 w/w %, based on the total composition, of a reacetylated chitosan having a molecular weight of not smaller than 100 kDa and a deacetylation degree of 40 to 70%, neutralized with an hydroxylated base, and 1 to 30 w/w %, based on the total composition, of a complexing agent selected from polyoses and polyols derived from polyoses. Said composition is useful for the preparation of an injectable formulation.

12 Claims, 5 Drawing Sheets

(51) Int. Cl.
*A61K 9/00* (2006.01)
*A61K 47/36* (2006.01)
*A61L 27/20* (2006.01)
*A61L 31/04* (2006.01)
*C08B 37/08* (2006.01)

(52) U.S. Cl.
CPC .............. *A61K 9/0024* (2013.01); *A61K 47/36* (2013.01); *A61L 27/20* (2013.01); *A61L 31/042* (2013.01); *C08B 37/003* (2013.01)
USPC ......................................................... 424/445

(56) References Cited

U.S. PATENT DOCUMENTS

| | | | |
|---|---|---|---|
| 5,773,608 | A | 6/1998 | Yen et al. |
| 6,156,348 | A * | 12/2000 | Santos et al. ................... 424/501 |
| 6,344,488 | B1 | 2/2002 | Chenite et al. |
| 2004/0047892 | A1 * | 3/2004 | Desrosiers et al. ........... 424/423 |
| 2004/0171151 | A1 * | 9/2004 | Domard et al. ................ 435/395 |
| 2005/0222332 | A1 * | 10/2005 | Nakagawa et al. ............ 525/104 |

FOREIGN PATENT DOCUMENTS

| | | |
|---|---|---|
| WO | WO-99/07416 | 2/1999 |
| WO | WO 99/07416 | 2/1999 |
| WO | WO 01/36000 A1 | 5/2001 |
| WO | WO-01/36000 A1 | 5/2001 |
| WO | WO 02078760 A1 * | 10/2002 |
| WO | WO-2005/097871 A1 | 10/2005 |
| WO | WO2005097871 A1 * | 10/2005 |

OTHER PUBLICATIONS

Sorlier et al., Relation between the Degree of Acetylation and the Electrostatic Properties of Chitin and Chitosan, Biomacromolecules, ACS, 2001, pp. 765-772, vol. 2.

International Search Report issued by the European Patent Office, dated Aug. 7, 2006, for International Application No. PCT/EP2005/013980; 4 pages.

Written Opinion issued by the European Patent Ofice, dated Aug. 7, 2006, for International Application No. PCT/EP2005/013980; 6 pages.

International Preliminary Report on Patentability, issued by The International Bureau of WIPO, Geneva, Switzerland, dated Jun. 24, 2008, for International Application No. PCT/EP2005/013980; 7 pages.

Emilie Patois, et al., Novel Thermosensitive Chitosan Hydrogels: In vivo Evaluation; *Journal of Biomedical Materials Research* Part A; pp. 324-330; published online Nov. 3, 2008 in Wiley InterScience (www.interscience.wiley.com); DOI: 10.1002/jbm.a.32211; © 2008 Wiley Periodicals, Inc.; 7 pages.

Claire Jury, et al., Irradiating or Autoclaving Chitosan/Polyol Solutions: Effect on Thermogelling Chitosans-β-glycerophosphate Systems; *Chemical & Pharmaceutical Bulletin*, 2002, 50(10); pp. 1335-1340; © 2002 Pharmaceutical Society of Japan (2008-546139); 7 pages.

* cited by examiner

A

B

THERMOSETTING NEUTRALIZED CHITOSAN COMPOSITION FORMING A HYDROGEL, LYOPHILIZATE, AND PROCESSES FOR PRODUCING THE SAME

This application is the national phase under 35 U.S.C. §371 of PCT International Application No. PCT/EP2005/013980 which has an International filing date of Dec. 23, 2005, which designated the United States of America, which is expressly incorporated by reference.

FIELD OF THE INVENTION

The present invention relates to an aqueous thermosetting neutralized chitosan composition forming a phosphate-free, transparent hydrogel at a temperature higher than 5° C., and to a process for producing the same.

Further, the present invention relates to a lyophilizate obtained by freeze-drying the thermosetting neutralized chitosan composition of the present invention and to a process for producing the same.

BACKGROUND OF THE INVENTION

Hydrogels are attractive for biomedical applications.

Further, hydrogels exhibiting the specific ability of increasing their viscosity with temperature, also called "thermosensitive/thermoresponsive/pseudothermosetting/thermogelling hydrogels", were proved to have a facilitated application combined with an increased residence time at the site of application, and therefore may be advantageously used for drug delivery or tissue augmentation.

As known from O. Felt et al. in The Encyclopedia of Controlled Drug Delivery, 1999, said thermosensitive hydrogels may be based advantageously on polymers of natural origin, for example on chitosan which is a commercially available inexpensive polymer derived from chitin, the second most abundant polysaccharide after cellulose.

Chitosan is known as a chitin derivative obtained by partial to substantial alkaline N-deacetylation of chitin also named poly(N-acetyl-D-glucosamine), which is a naturally occurring biopolymer.

Chitosan contains free amine (—$NH_2$) groups and may be characterized as to the proportion of N-acetyl-D-glucosamine units and D-glucosamine units, and such is expressed as the degree of deacetylation (DD) of the fully acetylated polymer chitin.

Parameters of chitosan influencing important properties such as solubility and viscosity are the degree of deacetylation (DD) which may be understood as representing the percentage of deacetylated monomers, and the molecular weight (Mw).

Chitosan is known to be biodegradable, biocompatible, bioadhesive, bacteriostatic, and further to promote wound-healing, drug absorption, and tissue reconstruction.

Due to its above mentioned intrinsic properties, chitosan is known to have numerous cosmetic and pharmaceutical activities, and has been also widely explored for various applications through gels.

Therefore, considering the advantageous properties of chitosan, there is a continuous need to improve the properties of known thermosensitive chitosan hydrogels which are still considered as very promising for a wider range of biomedical applications.

WO-A-99/07416 (BIOSYNTHEC) discloses a pH-dependent temperature-controlled chitosan hydrogel which has thermosensitive properties at neutral pH such that it has low viscosity at low temperature but gels at body temperature.

This thermosensitive chitosan hydrogel is prepared by neutralizing a commercial chitosan having a deacetylation degree of about 80% with mono-phosphate dibasic salts of polyols or sugars exemplified in particular by β-glycerophosphate (β-GP).

However, presence of β-GP in the hydrogel leads to the following disadvantages.

β-GP is a negatively charged entity that can react with a positively charged bioactive component, leading to its precipitation or to the disturbance of its liberation from the hydrogel.

Therefore, presence of β-GP renders chitosan/β-GP hydrogels inappropriate for use with numerous drugs.

Further, the properties of this hydrogel, such as gelation time and viscosity, depend on the concentration of β-GP and are therefore limited by the solubility of β-GP.

In particular, a high concentration of β-GP is required to have a low gelation time avoiding the rapid elimination of the hydrogel after its administration.

However, a high concentration of β-GP also decreases the mechanical properties of the hydrogel.

Therefore, the gelation time has to be balanced with the consistency of the hydrogel, and it is not possible to obtain gels that have both a low gelation time and a high viscosity, which would be a desirable combination of characteristics.

Also, a too high concentration of β-GP may induce the precipitation of the hydrogel at its administration site.

Further, said thermosensitive chitosan/β-GP hydrogels were found to be turbid, thus rendering their use inappropriate for particular applications such as ocular or topical administrations.

In addition, phosphate-containing materials may be inappropriate in terms of biocompatibility (G. Molinaro et al., *Biomaterials,* 23:2717-2722 (2002)).

In order to overcome the disadvantages of chitosan/β-GP hydrogels, it was proposed in WO-A-2005/097871 (UNIVERSITE DE GENEVE) a thermosetting neutralized chitosan composition forming a phosphate-free transparent hydrogel at a temperature higher than 5° C., said composition comprising an homogeneously reacetylated chitosan having a molecular weight of not smaller than 200 kDa, and a deacetylation degree of 30-60%, neutralized with an hydroxylated base.

WO-A-2005/097871 also disclose that said composition may further comprise 1,3-propanediol to modulate the viscoelastic properties of the hydrogel.

However, 1,3-propanediol is neither mentioned as "generally recognized as safe" (GRAS), nor recognized as an additive mentioned in US pharmacopoeia, European pharmacopoeia or Japanese pharmacopoeia so that its use is limited in biomedical applications.

Further, thermosetting neutralized chitosan compositions containing 1,3-propanediol lose their thermoresponsive properties upon lyophilization.

In view of the continuous heed to provide improved thermosensitive chitosan hydrogels for biomedical applications, the present inventors have continued their researches to overcome the disadvantages of the known thermosensitive hydrogels.

An object of the present invention is to provide an aqueous thermosetting neutralized chitosan composition forming a phosphate-free transparent hydrogel having improved properties and being acceptable for biomedical applications.

Another object of the present invention is to provide an aqueous thermosetting neutralized chitosan composition which may be stored easily and which preserves its thermogelling properties after storage.

Still another object of the present invention is to provide an aqueous thermosetting neutralized chitosan composition having a facilitated application, for example by injection using needles or minimally invasive techniques.

These objects are achieved by the present invention.

SUMMARY OF THE INVENTION

According to a first aspect, the present invention provides an aqueous thermosetting neutralized chitosan composition (herein, also called "composition of the present invention") as defined in independent claim 1 and its dependent claims 2-11.

According to a second aspect, the present invention provides a lyophilizate of the aqueous thermosetting composition according to the first aspect, as defined in independent claim 12.

According to a third aspect, the present invention provides a process for producing the aqueous thermosetting neutralized chitosan composition according to the first aspect, as defined in independent claim 13 and its dependent claims 14-15.

According to a fourth aspect, the present invention provides a process for producing the lyophilizate according to the second aspect, as defined in independent claim 16.

According to a fifth aspect, the present invention provides the use of the composition according to the first aspect, or lyophilizate according to the second aspect, as defined in independent claims 17-20.

According to the present invention, adding a complexing agent selected from polyoses and polyols derived from polyoses to a specified chitosan composition allows advantageously to provide a phosphate-free transparent hydrogel having improved properties, which is acceptable for biomedical applications and which can be easily stored.

Other advantages of the present invention will appear in the following description.

The present invention will be now described in a more detailed manner.

DETAILED DESCRIPTION OF THE PRESENT INVENTION

Figure 1:
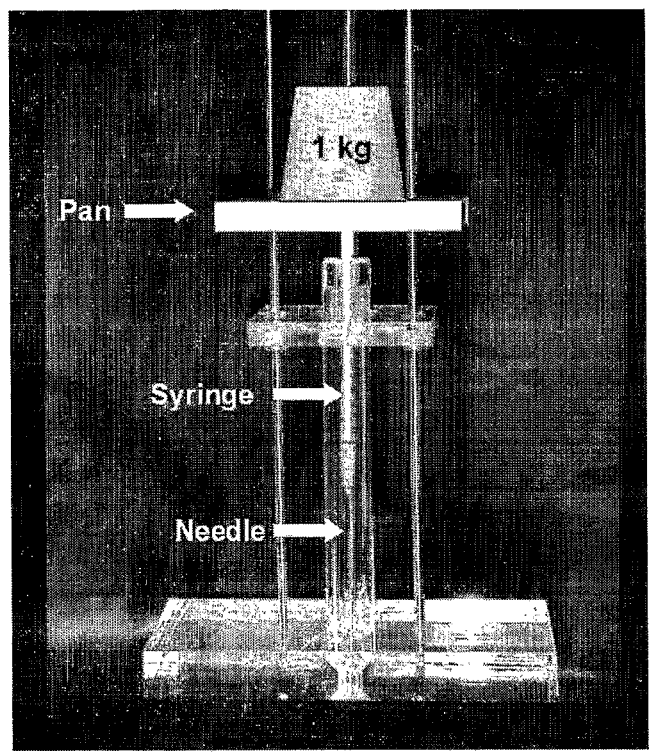
FIG. 1 shows a device for measuring the injectability of the composition of the present invention.

It is to be noted that in the present description and claims, the expression "thermosetting" in connection with the composition of the present invention means that temperature does not induce the gelation of the composition but acts rather as a catalyst which dramatically shortens the gelation time when risen.

It is also to be noted that in the present description, the expression "hydrogel" or "hydrogel of the present invention" is used instead of "composition of the present invention" when appropriate.

It is still to be noted that in the present description and claims, the term "neutralized" means a pH of 6.7-7.1.

According to the present invention, the aqueous thermosetting neutralized chitosan composition forming a phosphate-free transparent hydrogel at a temperature higher than 5° C. comprises a reacetylated chitosan neutralized with an hydroxylated base and a complexing agent selected from polyoses and polyols derived from polyoses.

The average molecular weight (Mw) of the reacetylated chitosan comprised in the composition of the present invention is typically not lower than 100 kDa.

Molecular weight of chitosan may be determined by asymmetrical flow field-flow fractionation (AFFF) coupled to multiangle light scattering (MALS) as reported for example by B. Wittgren and K.-G. Wahlund in *Journal of Chromatography A* 760:205-215 (1997).

Reacetylated chitosan having a Mw typically not lower than 100 KDa is particularly appropriate for use in the present invention because it allows the formation of a thermosetting composition forming a firm hydrogel.

Preferably, the reacetylated chitosan used in the present invention has a Mw not lower than 200 kDa.

The upper limit of the Mw of the reacetylated chitosan used in the present invention depends on the amount of the reacetylated chitosan comprised in the composition of the present invention and is determined by the ease of administration, which depends on the chosen application.

Reacetylated chitosan used in the present invention must have a deacetylation degree of 40-70% which means that the chitosan comprises 40 to 70% of D-glucosamine units and 60 to 30% of neutral N-acetyl-D-glycosamine units, respectively.

The deacetylation degree of chitosan may be determined by Nuclear Magnetic Resonance such as described in the literature by Lavertu et al., *Journal of Pharmaceutical and Biomedical Analysis* 32: 1149-1158 (2003).

If deacetylation degree of the reacetylated chitosan is lower than 40%, the reacetylated chitosan becomes a polymer close to chitin that is insoluble in acidic conditions and consequently not usable in the present invention.

If deacetylation degree of the reacetylated chitosan is higher than 70%, the reacetylated chitosan does not allow the preparation of a composition forming a phosphate-free transparent hydrogel.

Preferably, the deacetylation degree of the reacetylated chitosan comprised in the composition of the present invention is from 45 to 65%.

A reacetylated chitosan having a molecular weight typically not smaller than 100 kDa and a deacetylation degree of 40-70% for use in the present invention may be prepared for example according to the process disclosed in WO-A-2005/097871 or may be obtained from Novamatrix (Oslo, Norway).

The amount of the reacetylated chitosan comprised in the composition of the present invention must be from 0.1 to 5.0 w/w %, based on the total composition.

An amount of reacetylated chitosan lower 0.1 w/w % does not allow the formation of a hydrogel and an amount of reacetylated chitosan higher than 5.0 w/w % induces the formation of a composition too difficult to inject.

The amount of reacetylated chitosan comprised in the composition of the present invention will be chosen depending on the Mw of the chitosan and on the aimed application.

Preferably, the amount of the reacetylated chitosan comprised in the composition of the present invention is from 0.5 to 3.0 w/w %, based on the total composition.

The amount of the complexing agent comprised in the composition of the present invention must be from 1 to 30 w/w %, based on the total composition, and will depend on the concentration and molecular weight of the reacetylated chitosan as well as on the required gelation time and degree of consistency of the hydrogel.

The amount of the complexing agent comprised in the composition of the present invention is preferably from 5 to 15 w/w %, based on the total composition.

Said complexing agent selected from polyoses and polyols derived from polyoses comprised in the composition of the present invention allows to modulate the properties of the hydrogel, such as gelation time and viscosity of the hydrogel.

In one preferred embodiment of the present invention, the complexing agent which may be used in the present invention is a polyose, more preferably a polyose selected from monosaccharides and disaccharides.

As preferred examples of monosaccharides which may be used in the present invention, there may be cited D-glucose (also called dextrose), fructose and tagatose, which are known as excipients for pharmaceutical compositions according to European, US or Japanese pharmacopoeias.

As preferred examples of disaccharides which may be used in the present invention, there may be cited trehalose, sucrose, maltose and lactose which are known as excipients for pharmaceutical compositions according to European, US or Japanese pharmacopoeias, with trehalose being particularly preferred.

As other examples of polyoses which may be used in the present invention, there may be cited polysaccharides selected from polydextose and amylose which are known as excipients for pharmaceutical compositions.

In another preferred embodiment of the present invention, the complexing agent which may be used in the present invention is a polyol derived from polyose (also called sugar alcohol) selected from glycerol, mannitol, sorbitol, xylitol, erythritol, lactitol and maltitol, which are known as excipients for pharmaceutical compositions according to European, US or Japanese pharmacopoeias, with glycerol being particularly preferred.

The compositions of the present invention may be freezed for storage while preserving their thermogelling properties and have to be thawed at 4° C. before their use.

Further, the compositions of the present invention, except those comprising glycerol as the complexing agent, may be advantageously freeze-dried to obtain a lyophilizate for facilitated storage and distribution, and reconstituted by the addition of cooled water to the lyophilizate under stirring at 4° C. before their use, while preserving their thermogelling properties.

The composition of the present invention may be prepared according to a process forming part of the present invention.

In step a) of said process, the reacetylated chitosan having a molecular weight typically not smaller than 100 kDa, preferably not smaller than 200 kDa, a deacetylation degree of 40-70%, preferably 45-65%, is solubilized in an aqueous HCl medium and after complete dissolution of chitosan, the temperature of the chitosan solution is cooled down to a temperature lower than 5° C., for example in an ice bath.

Then, in step b) of said process, the pH of the cooled chitosan solution is neutralized until the pH 6.7-7.1, preferably pH 6.8, by adding dropwise, under stirring at a temperature lower than 5° C., the required amount of an aqueous solution containing a hydroxylated base previously cooled to a temperature lower than 5° C.

A higher pH is not appropriate since it would induce the precipitation of chitosan.

According to said process, the hydroxylated base used for neutralization is preferably NaOH.

Inadequate stirring or too fast addition of aqueous hydroxylated base induces the precipitation of the chitosan.

In step c) of said process, the complexing agent selected from polyoses and polyols derived from polyoses is added during or after the solubilization step a), or before, during or after the neutralization step b).

It is pointed out that the description referring to chitosan, complexing agent and amounts thereof in connection with the composition of the present invention also applies in connection with the process of the present invention.

The process for preparing the composition of the present invention may further comprise, if required, a step of sterilizing the reacetylated chitosan before the step a) of solubilization. To obtain a sterile hydrogel, the preparation is performed under aseptic conditions (e.g. under a laminar flow) and every added solution is previously filtered through a 0.22 µm filter or steam-sterilized.

For example, sterilization may be performed by radiation or ideally by steam sterilization of reacetylated chitosan suspended in water, as described by Yen (Yen S. F. et al., 1998, U.S. Pat. No. 5,773,608).

The process for preparing the composition of the present invention may further comprise, if required a step of freezing said composition for facilitated storage.

In this case, the freezed composition has to be thawed at 4° C. before its use.

In a particularly preferred embodiment, the process according to the present invention may be completed by further freeze-drying the composition of the present invention, except the composition of the present invention containing glycerol as the complexing agent, to obtain a lyophilizate forming part of the present invention.

Said lyophilizate may be conveniently stored and distributed for medical use, and may be reconstituted by the addition of cold water under stirring at 4° C.

When the temperature of the thermosetting neutralized chitosan composition of the present invention is increased, for example after administration, thermogelation occurs leading to the formation of a phosphate-free, transparent firm hydrogel. The higher is the temperature, the shorter is the gelation time.

According to the present invention, the composition of the present invention may be advantageously used as a drug delivery system and in view of its specific properties, may be advantageously used for the preparation of an injectable formulation.

Further, since the lyophilizate of the present invention preserves its thermogelling properties after reconstitution, it may be advantageously used for the preparation of a drug delivery system and for the preparation of an injectable formulation.

In order to demonstrate the improved elastic properties of the phosphate-free transparent chitosan hydrogels of the present invention, rheological measurements of various hydrogels according to the present invention and comparative hydrogels were performed according to the following method, unless otherwise indicated.

Viscoelastic properties of hydrogels were determined immediately after preparation of the hydrogels using a Rheostress 1 (Haake, Karlsruhe, Germany) using a cone/plate device (diameter 60 mm, angle 4°). Temperature was controlled with a thermostatic bath Haake DC 30 and a cooling device Haake K10 (Haake, Karlsruhe, Germany) coupled with the rheometer. Hydrogels were placed between the cone and plate (cooled down at 4° C.) and measured after 10 minutes. All measurements were performed in the linear viscoelastic range and G' (storage modulus) and G" (loss modulus) were determined under a constant deformation ($\gamma=0.05$) at 1.00 Hz for 180 minutes. The temperature was increased from 4 to 37° C. at 6.6° C./min over the first 5 minutes, and maintained at 37° C. over the following 175 minutes. Evaporation of water leading to drying of hydrogels was minimized by use of a cover surrounding the cone/plate device.

Figure 2:
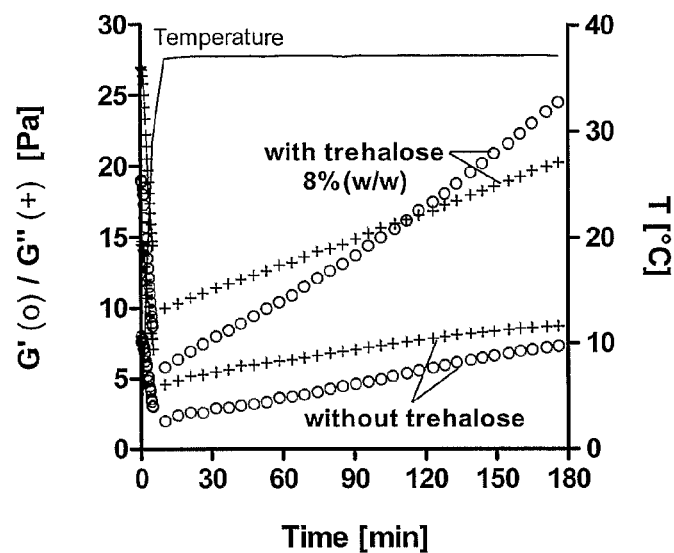
FIG. 2 shows the evolution of the elastic modulus G' (storage modulus) and of the viscous modulus G" (loss modulus) of the transparent hydrogel containing trehalose obtained in Example 1, as compared with the same hydrogel without trehalose, as a function of time when the temperature increases from 4 to 37° C.
Figure 3:
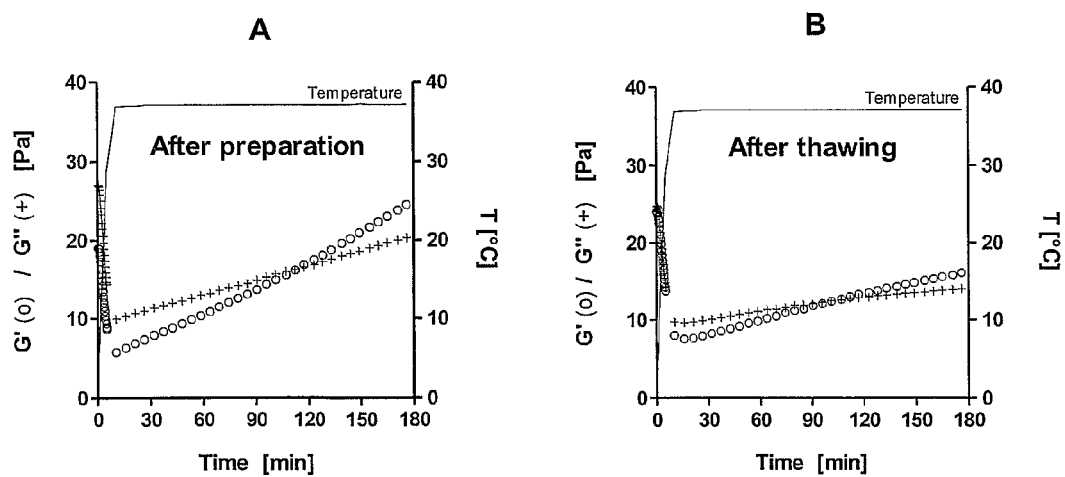
FIG. 3 shows the evolution of the elastic modulus G' (storage modulus) and of the viscous modulus G" (loss modulus) of the transparent hydrogel containing trehalose obtained in Example 1, after preparation (A) and after thawing (B), as a function of time when the temperature increases from 4 to 37° C.
Figure 4:
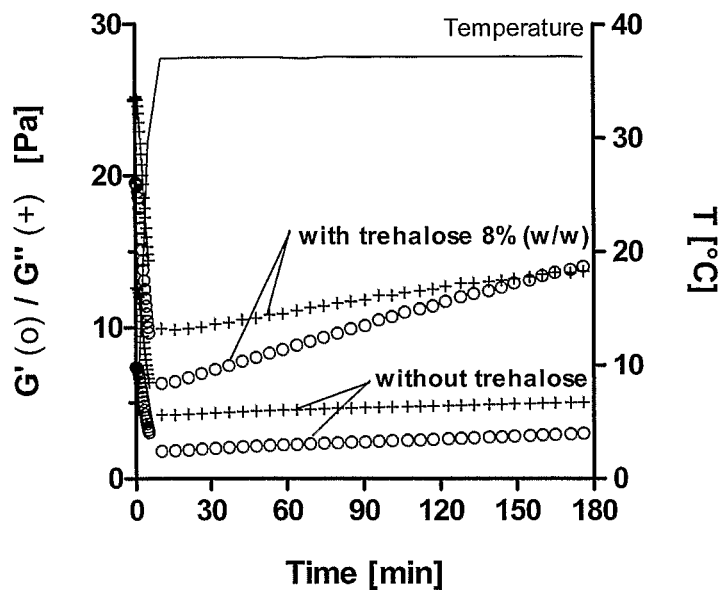
FIG. 4 shows the evolution of the elastic modulus G' (storage modulus) and of the viscous modulus G" (loss modulus) of the transparent hydrogel containing trehalose obtained in Example 1, after freeze-drying and reconstitution, as compared with the same hydrogel without trehalose, as a function of time when the temperature increases from 4 to 37° C.
Figure 5:
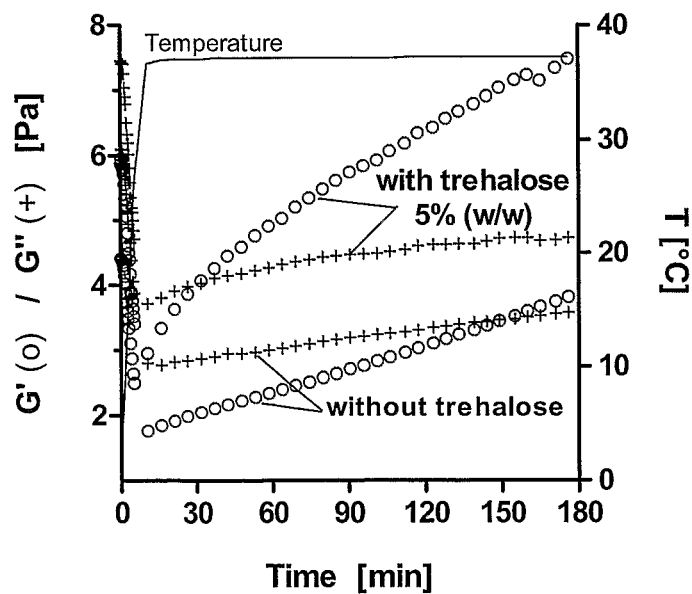
FIG. 5 shows the evolution of the elastic modulus G' (storage modulus) and of the viscous modulus G" (loss modulus) of the transparent hydrogel containing trehalose obtained in Example 4, as compared with the same hydrogel without trehalose, as a function of time when temperature increases from 4 to 37° C.
Figure 6:
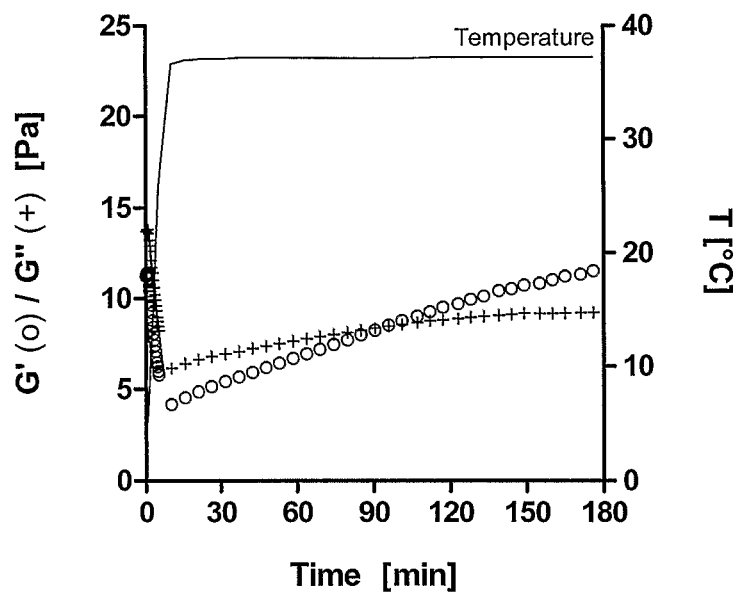
FIG. 6 shows the evolution of the elastic modulus G' (storage modulus) and of the viscous modulus G" (loss modulus) of the transparent hydrogel containing 1,3-propanediol obtained in Example 5 (Comparative), after preparation (A) and after freeze-drying and reconstitution (B), as a function of time when the temperature increases from 4 to 37° C.
Figure 6:
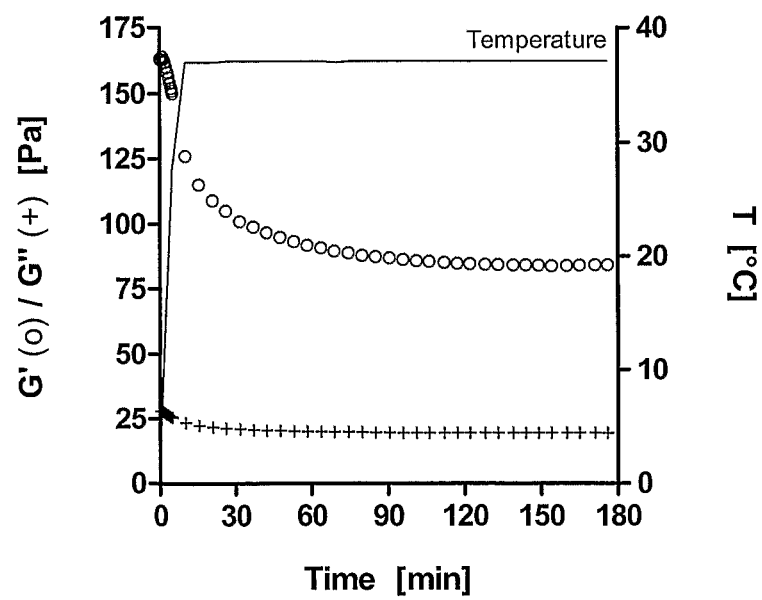
Figure 7:
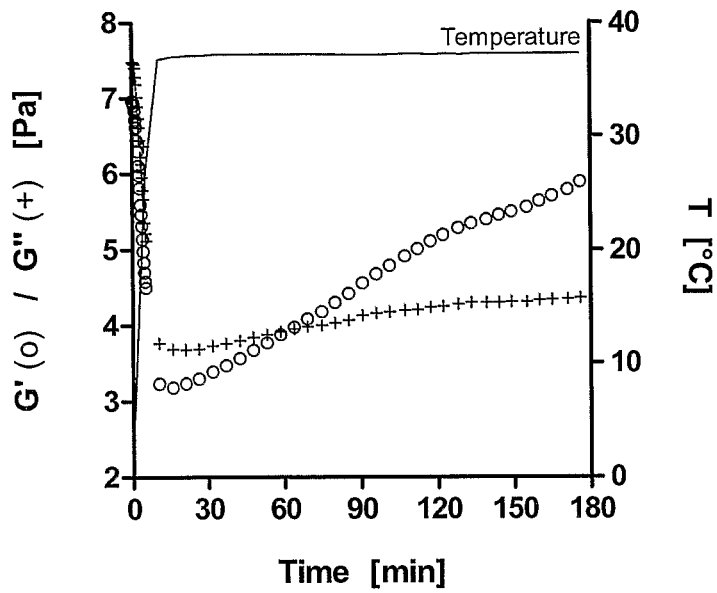
FIG. 7 shows the evolution of the elastic modulus G' (storage modulus) and of the viscous modulus G" (loss modulus) of the transparent hydrogel containing mannitol obtained in Example 6, after freeze-drying and reconstitution, as a function of time when the temperature increases from 4 to 37° C.
Figure 8:
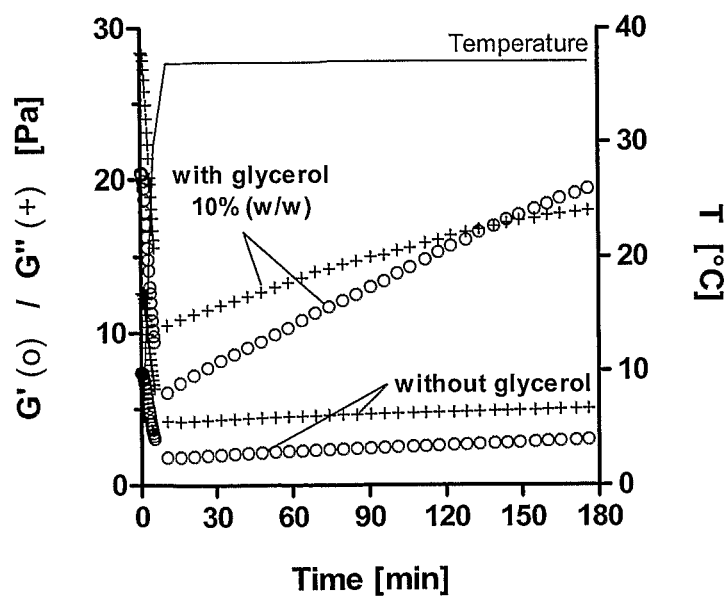
FIG. 8 shows the evolution of the elastic modulus G' (storage modulus) and of the viscous modulus G" (loss modulus) of the transparent hydrogel containing glycerol obtained in Example 7, as a function of time when the temperature increases from 4 to 37° C.

The following hydrogels have been tested:

(1) the hydrogel of the present invention obtained in Example 1, containing 2 w/w % of chitosan (DD=47%) obtained from Novamatrix and 8 w/w % trehalose, and the comparative hydrogel without trehalose (see FIG. 2);

(2) the hydrogel of the present invention obtained in Example 1, containing 2 w/w % of chitosan (DD=47%) obtained from Novamatrix and 8 w/w % trehalose, after preparation and after freezing-thawing according to Example 2 (see FIGS. 3A and 3B);

(3) the hydrogel of the present invention obtained in Example 1, containing 2 w/w % of chitosan (DD=47%) obtained from Novamatrix and 8 w/w % trehalose, after freeze-drying and reconstitution according to Example 3, and the comparative hydrogel without trehalose (see FIG. 4);

(4) the hydrogel of the present invention obtained in Example 4, containing 0.9% w/w of chitosan (DD=61%) obtained according to Preparation Example 1, and 5 w/w % trehalose, and the comparative hydrogel without trehalose (see FIG. 5);

(5) a comparative hydrogel obtained in Example 5 (Comparative), containing 1 w/w % chitosan (DD 47%) obtained according to Preparation Example 2 and 10 w/w % 1,3-propanediol, after preparation and after freeze-drying and reconstitution (see FIGS. 6A and 6B);

(6) the hydrogel of the present invention obtained in Example 6, containing 0.9 w/w % chitosan (DD=61%) obtained according to Preparation Example 1, and 5 w/w % mannitol, after freeze-drying and reconstitution (see FIG. 7);

(7) the hydrogel of the present invention obtained in Example 7, containing 2 w/w % chitosan (DD 47%) obtained from Novamatrix and 10% glycerol, and the comparative hydrogel without glycerol (see FIG. 8).

FIGS. 2-8 show the evolution of the elastic modulus G' (storage modulus) and of the viscous modulus G" (loss modulus) of the tested hydrogels as a function of time when temperature increases from 4 to 37° C. The onset of incipient formation of the gel network, which defines the gelation time, is given by the time of crossover of G' and G".

As shown in FIG. 2, addition of a polyose such as trehalose according to the present invention increases the G' and G" values of the hydrogel as compared with the same hydrogel without trehalose.

FIG. 3A shows the viscoelastic properties of the hydrogel just after its preparation (as reported in FIG. 2) while FIG. 3B shows the viscoelastic properties of the same hydrogel after freezing and thawing.

As shown in FIG. 3B, thermogelling properties of the composition of the present invention are maintained after freezing and thawing.

FIG. 4 shows the viscoelastic properties of the hydrogel reported in FIG. 2 after freeze-drying and reconstitution.

As shown in FIG. 4, thermogelling properties of the composition of the present invention are maintained after freeze-drying and reconstitution.

As shown in FIG. 5, the composition of the present invention containing trehalose shows a gelification point of 30 minutes, whereas the same formulation containing no trehalose forms a gel after 150 minutes.

As shown in FIGS. 6A and 6B, the comparative composition containing 1,3-propanediol forms an hydrogel when the viscoelastic properties are measured after its preparation (FIG. 6A) but does not preserve its thermogelling properties after lyophilization and reconstitution as indicated by the absence of a gelification point in FIG. 6B.

As shown in FIG. 7, the composition of the present invention containing mannitol preserves its thermogelling properties after lyophilization and reconstitution, as indicated by the presence of a gelification point.

As shown in FIG. 8, the composition of the present invention containing glycerol forms an hydrogel, as indicated by the presence of a gelification point whereas the same formulation containing no glycerol shows no gelification point after 180 minutes.

The following examples are intended to illustrate the present invention. However, they cannot be considered in any case as limiting the scope of the present invention.

EXAMPLES

In the following examples, the deacetylation degree of chitosans was determined by Nuclear Magnetic Resonance (NMR) such as described in the literature by Lavertu et al., *Journal of Pharmaceutical and Biomedical Analysis* 32: 1149-1158 (2003).

The molecular weight of chitosans was determined by asymmetrical flow field-flow fractionation (AFFF) coupled to multiangle light scattering (MALS), as follows:

Fractionation of the chitosan solution (2 mg/ml in acetate buffer pH 4.5) was performed in a trapezoidal channel, 26.5 cm in length and 350 µm in height, connected to an Eclipse F system (Wyatt Technology Europe, Dembach, Germany). The bottom of the channel was lined with a regenerated cellulose membrane with a 10 kDa cut-off (Microdyn-Nadir GmbH, Wiesbaden, Germany). The elution medium consisted of acetate buffer pH 4.5. The channel flow was set to 1 ml/min and the injection flow to 0.2 ml/min. The separation started with a focus flow of 1 ml/min for 3 minutes and was followed by a cross flow of 0.2 ml/min for 15 minutes. A Dawn EOS multi-angle light scattering detector (Wyatt Technology, Santa Barbara, USA) and a refractive index (RI) detector (Waters differential refractometer, Milford, Mass., USA) were coupled online with the field-flow fractionation channel. The light scattering detector was equipped with a GaAs laser (wavelength: 690 nm) and eighteen detectors. Scattered light was collected at angles comprised between 14 and 163 degrees. The RI detector was calibrated with sodium chloride. Data were collected and analysed with the Astra version 4.90.08 software, using a refractive index increment (dn/dc) of 0.153 ml/g.

In the following examples, injectability of some compositions was determined with a device composed of a vertical support for a 1.0 ml luer lock syringe filled with the hydrogel at 3° C. and a pan resting on the piston of the syringe as shown in FIG. 1. A 27 $G^{1/2} \times 0.5$ inches needles was fixed on the syringe which was positioned in the support. A mass (500 gr or 1 kg) was placed on this pan and the time necessary for the composition to be expelled from the syringe was measured.

In the following Examples 1-3 and 7, the reacetylated chitosan used for the preparation of the hydrogel is a reacetylated chitosan obtained from Novamatrix (batch FU-507-03), with a DD of 47% (measured by NMR) and an average molecular weight (Mw) of 3600 kDa (measured by AFFF-MALS).

In the following Examples 4 and 6, the reacetylated chitosans used for the preparation of the hydrogels are reacetylated chitosans prepared according to Preparation Example 1.

In the following Example 5, the reacetylated chitosan used for the preparation of the hydrogel is reactetylated chitosan prepared according to Preparation Example 2.

PREPARATION EXAMPLE 1

Preparation of a Reacetylated Chitosan "Fagal Lot 21" Having a DD of 61% According to the Method Disclosed in WO-A-2005/097871

25.5 gr of chitosan flakes (Sigma-aldrich, Saint Louis, Mo., USA, product number 41,941-9, batch 14418LB) were dissolved in 1 liter of a solution of acetic acid 10% and methanol (50/50) for one hour under stirring. 550 ml of methanol were added. After 2 hours stirring, the mixture was filtered through a 100 µm filter to eliminate insoluble particles. The viscous solution was then dialyzed (Spectra/Por® 1 Dialysis Membranes 6,000-8,000 MWCO, no 132665, Spectrum Laboratories, Rancho Dominguez, USA) against deionized water for 72 hours, with daily change of the water. The solution was then filtered through a 5 µm filter.

Under stirring, 400 ml of NH$_4$OH 0.2M/methanol (50/50) were added to induce precipitation. After 1 hour stirring, the suspension was filtered through a 100 µm filter. The precipitate was washed with methanol until neutral. The purified chitosan obtained was dried in the presence of Silicagel, under vacuum, at room temperature and protected from light.

10 g of this purified chitosan were dissolved in 500 ml acetic acid 10%/methanol (50/50). The mixture was stirred for 1 hour and allowed to stand overnight. 400 ml of methanol were added. The solution was stirred for several hours and allowed to stand overnight. 150 ml of methanol were added and the chitosan solution was cooled down to a temperature lower than 5° C. using an ice bath. A solution made of 2.4 ml acetic anhydride and 200 ml methanol was cooled down to a temperature lower than 5° C. and added dropwise to the chitosan solution, under vigorous mechanical stirring. This solution containing homogeneously reacetylated chitosan was kept under stirring at a temperature lower than 5° C. for one hour to ensure complete reaction, and allowed to stand overnight at room temperature. To eliminate salts produced during reacetylation and to further eliminate insoluble particles, this viscous solution was dialyzed against deionized water for 12 days (same dialysis membranes as above) with daily change of the water. The chitosan viscous solution was then filtered through a 5 µm filter. 200 ml of NH$_4$OH 0.2M/methanol (50/50) were added under stirring to induce chitosan precipitation. After 4 hours stirring, the chitosan was passed through a 100 µm filter and washed with methanol. Finally, the homogeneously reacetylated chitosan was dried in the presence of Silicagel, under vacuum, at room temperature and protected from light.

The obtained reacetylated chitosan had a DD of 61% (measured by NMR) and an average molecular weight (Mw) of 7900 kDa (measured by AFFF-MALS).

PREPARATION EXAMPLE 2

Preparation of a Reacetylated Chitosan "Fagal Lot 25" Having a DD of 47% According to the Method Disclosed in WO-A-2005/097871

Chitosan flakes (Sigma-aldrich, Saint Louis, Mo., USA, product number 41,941-9, batch 14418LB) were purified as in Preparation Example 1. Chitosan was then reacetylated with a solution made of 2.0 ml acetic anhydride and 200 ml methanol according to the same procedure as in Example Preparation 1.

The obtained reacetylated chitosan had a DD of 47% (measured by NMR).

Example 1

Preparation of a Composition According to the Present Invention, Containing 2% w/w of Reacetylated Chitosan (DD=47%$_{RMN}$) Provided by Novamatrix and 8 w/w % Trehalose 700 mg of reacetylated chitosan provided by Novamatrix (batch FU-507-03), with a DD of 47% (measured by RMN) were autoclaved in suspension in water at a concentration of 4% (w/w). 145 µl HCl were added and the suspension was kept under stirring for 18 h at room temperature to allow complete chitosan solubilization. 3.09 g of trehalose were solubilized in 6.5 ml NaOH 0.15M. This solution was cooled down in an ice bath and added dropwise under stirring to the cooled down chitosan solution. The pH of the gel was then adjusted to 6.8 by dropwise addition of cooled down diluted NaOH. Finally, cold water was added to obtain a total mass of 35 g. The transparent hydrogel obtained showed an increase of its viscoelastic behaviour following time at 37° C., as illustrated in FIG. 2 and FIG. 3A and had a gelation of time of 111 min. The injectability measurement gave 30 seconds with a kilogram mass.

Example 2

Freezing-Thawing the Hydrogel Obtained in Example 1

10 gr of the preparation of Example 1 was frozen in liquid nitrogen and kept at −20° C. It was then thawed at 4° C. before its rheological properties were determined. As shown in FIG. 3B, the thermogelling properties were maintained.

Example 3

Freezing-Drying the Hydrogel Obtained in Example 1

10 gr of the preparation of Example 1 was frozen in liquid nitrogen and kept at −20° C. before being lyophilized for 24 hours with an Edwards Modulyo Freeze dryer (plate at −50° C., vacuum of $10^{-1}$ mbar). The lyophilizate obtained was reconstituted by the addition of cold water under stirring, at 4° C. As shown in FIG. 4, the thermogelling properties were maintained.

Example 4

Preparation of a Composition According to the Present Invention, Containing 0.9% w/w of Reacetylated Chitosan "Fagal Lot 21" (DD=61%$_{RMN}$) Obtained According to the Preparation Example 1 and 5 w/w % Trehalose 270 mg of reacetylated chitosan prepared according to Preparation Example 1 and having a DD of 61% (measured by RMN) were solubilized in 15 ml HCl 0.1N under stirring for 18 hours at room temperature. 1.66 g of trehalose dihydrate were solubilized in 8 ml NaOH 0.15M. This solution was cooled down in an ice bath and added dropwise under stirring, to the cooled down chitosan solution. The pH of the gel was then adjusted to 6.8 by dropwise addition of cooled down diluted NaOH. Finally, cold water was added to obtain a total mass of 30 g. The transparent hydrogel obtained showed an increase of its viscoelastic behaviour following time at 37° C., as illustrated in FIG. 5. The formulation containing trehalose showed a gelification point after 30 minutes, whereas the formulation containing no trehalose formed a gel after 150 minutes. The injectability measurement gave 30 seconds with a 500 gr mass.

Example 5 (Comparative)

Preparation of a Comparative Composition Containing 1% w/w of Reacetylated Chitosan "Fagal Lot 25" (DD=47%$_{RMN}$) Obtained According to the Preparation Example 2 and 10 w/w % 1,3-propanediol 200 mg of reacetylated chitosan prepared according to Preparation Example 2 and having a DD of 47% (measured by RMN) were solubilized in 10 ml HCl 0.1N under stirring for 18 hours at room temperature. 2 g of cooled down 1,3-propanediol were added to the solubilized chitosan. The pH of the gel was then adjusted to 6.8 by dropwise addition of cooled down diluted NaOH. Finally, cold water was added to obtain a total mass of 20 g. The transparent hydrogel obtained showed an increase of its viscoelastic behaviour following time at 37° C., as illustrated in FIG. 6A.

When frozen (at −80° C.), lyophilized (for 24 hours) and reconstituted with cold water under stirring at 4° C., the preparation obtained was not any longer injectable ($27G^{1/2}$, a kilogram mass) in the injectability measurement test. Moreover, it did not present any thermogelling properties, as shown in FIG. 6B.

Example 6

Preparation of a Composition According to the Present Invention, Containing 0.9% w/w of Reacetylated Chitosan "Fagal Lot 21" (DD=61%$_{RMN}$) obtained according to the Preparation Example 1 and 5 w/w % mannitol 630 mg of the reacetylated chitosan obtained according to Preparation Example 1 were solubilized in 35 ml HCl 0.1N under stirring for 18 hours at room temperature. This chitosan solution was cooled down to around 5° C. before adding 3.5 g of mannitol. The pH of the gel was then adjusted to 6.8 by dropwise addition of cooled down diluted NaOH. Finally, cold water was added to obtain a total mass of 70 g. 10 g of this preparation were frozen in liquid nitrogen and kept at −20° C. before being lyophilized for 24 hours with an Edwards Modulyo Freeze dryer (plate at −50° C., vacuum of $10^{-1}$ mbar). The lyophilizate obtained was reconstituted by the addition of cold water under stirring, at 4° C. The transparent hydrogel obtained showed an increase of its viscoelastic behaviour following time at 37° C., with a gelation time of 1 hour, as illustrated in FIG. 7.

Example 7

Preparation of a Composition According to the Present Invention, Containing 2% w/w of Reacetylated Chitosan (DD=47%$_{RMN}$) Provided by Novamatrix and 10 w/w % of Glycerol 700 mg of reacetylated chitosan obtained from Novamatrix were autoclaved in suspension in water at a concentration of 4% (w/w). After cooling down the suspension at room temperature, 145 µl HCl were added and the mixture was kept under stirring for 18 h to allow complete chitosan solubilization. The chitosan solution was cooled down to around 5° C. using an ice bath and 3.5 g of cooled down glycerol were added. The pH of the gel was then adjusted to 6.8 by dropwise addition of cooled down diluted NaOH. Finally, cold water was added to obtain a total mass of 35 g. The transparent hydrogel containing glycerol showed an increase of its viscoelastic behaviour following time at 37° C. with a gelation time of 135 minutes, as illustrated in FIG. 8, whereas the formulation containing no glycerol showed no gelification point after 180 minutes.

The invention claimed is:

1. An aqueous thermosetting neutralized chitosan composition forming a phosphate-free transparent hydrogel at a temperature higher than 5° C., said composition comprising 0.1 to 5.0 w/w %, based on the total composition, of a reacetylated chitosan having a molecular weight of not smaller than 100 kDa and a deacetylation degree of 40 to 70%, neutralized until a pH of 6.7-7.1, under a temperature lower than 5° C. with an hydroxylated base previously cooled to a temperature lower than 5° C., and 1 to 30 w/w %, based on the total composition, of a complexing agent selected from polyoses and sugar alcohols suitable for pharmaceutical use; wherein the said aqueous composition can be lyophilized into a powder which can be then rehydrated into an aqueous thermosetting composition which still forms a phosphate free, transparent hydrogel at a temperature greater than 5° C. after lyophilization and rehydration.

2. The aqueous thermosetting neutralized chitosan composition according to claim 1, wherein the reacetylated chitosan is comprised in an amount of 0.5 to 3.0 w/w %, based on the total composition.

3. The aqueous thermosetting neutralized chitosan composition according to claim 1, wherein the deacetylation degree of the reacetylated chitosan is 45 to 65%.

4. The aqueous thermosetting neutralized chitosan composition according to claim 1, wherein the molecular weight of the reacetylated chitosan is not smaller than 200 kDa.

5. The aqueous thermosetting neutralized chitosan composition according to claim 1, wherein the complexing agent is comprised in an amount of 5 to 15 w/w %, based on the total composition.

6. The aqueous thermosetting neutralized chitosan composition according to claim 1, wherein the complexing agent is a polyose.

7. The aqueous thermosetting neutralized chitosan composition according to claim 6, wherein the polyose is selected from monosaccharides and disaccharides.

8. The aqueous thermosetting neutralized chitosan composition according to claim 7, wherein the polyose is a monosaccharide selected from D-glucose, fructose and tagatose.

9. The aqueous thermosetting neutralized chitosan composition according to claim 7, wherein the polyose is a disaccharide selected from trehalose, sucrose, maltose and lactose.

10. The aqueous thermosetting neutralized chitosan composition according to claim 9, wherein the disaccharide is trehalose.

11. The aqueous thermosetting neutralized chitosan composition according to anyone of claims 1 to 5, wherein the complexing agent is a sugar alcohol selected from the group consisting of: glycerol, mannitol, sorbitol, xylitol, erythritol, lactitol and maltitol.

12. A lyophilizate obtained by freeze-drying the aqueous thermosetting neutralized chitosan composition of anyone of claims 1 to 11, except the composition containing glycerol as the complexing agent.

* * * * *